(12) United States Patent
Bailey et al.

(10) Patent No.: US 11,813,098 B2
(45) Date of Patent: Nov. 14, 2023

(54) TRANSLATION DRIVE SYSTEM FOR AN IMAGING SYSTEM

(71) Applicant: Siemens Medical Solutions USA, Inc., Malvern, PA (US)

(72) Inventors: Eric M. Bailey, North Hampton, NH (US); Andrew Tybinkowski, Topsfield, MA (US); Jeffrey Johnson, West Newbury, MA (US); Jamie Brooks, Amesbury, MA (US); Mark Dieselman, Amesbury, MA (US); Clayton Garland, Barrington, NH (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 312 days.

(21) Appl. No.: 17/292,804

(22) PCT Filed: Oct. 24, 2019

(86) PCT No.: PCT/US2019/057755
§ 371 (c)(1),
(2) Date: May 11, 2021

(87) PCT Pub. No.: WO2020/106403
PCT Pub. Date: May 28, 2020

(65) Prior Publication Data
US 2021/0393221 A1  Dec. 23, 2021

Related U.S. Application Data

(60) Provisional application No. 62/769,088, filed on Nov. 19, 2018, provisional application No. 62/769,101, filed on Nov. 19, 2018.

(51) Int. Cl.
*A61B 6/00* (2006.01)
*A61B 6/03* (2006.01)

(52) U.S. Cl.
CPC ............ *A61B 6/4476* (2013.01); *A61B 6/035* (2013.01); *A61B 6/44* (2013.01)

(58) Field of Classification Search
CPC ......... A61B 6/035; A61B 6/44; A61B 6/4476; A61B 6/4411; A61B 6/04; A61B 6/0407;
(Continued)

(56) References Cited

U.S. PATENT DOCUMENTS 4,645,933 A * 2/1987 Gambini ................ A61B 6/037
250/363.08
4,928,283 A * 5/1990 Gordon ................. A61B 6/032
250/363.05
(Continued)

FOREIGN PATENT DOCUMENTS

| DE | 102012201529 A1 | 5/2013 |
| EP | 2984989 A1 | 2/2016 |
| WO | 2008142695 A1 | 11/2008 |

*Primary Examiner* — Dani Fox
*Assistant Examiner* — Soorena Kefayati

(57) ABSTRACT

A translation drive system for an imaging system having an imaging gantry and a gantry base. The system includes at least one upper rail affixed to the imaging gantry and at least one lower rail affixed to the base, wherein the lower rail includes a stop. The system also includes front and lower carriages moveably attached to the lower rail wherein the upper rail is moveably attached to an upper carriage to enable movement of the imaging gantry relative to the base. Further, the system includes an extension spring attached between the lower carriage and the imaging gantry wherein when a lower carriage rear surface contacts the stop, the upper rail moves horizontally past a base rear surface into an extended position wherein the imaging gantry extends horizontally beyond the base rear surface. The system also includes a linear actuator located in the base that moves the imaging gantry.

20 Claims, 6 Drawing Sheets

(58) Field of Classification Search
CPC ....... A61B 6/4405; A61B 6/0487; A61B 6/03; A61B 6/032; A61B 6/4452
See application file for complete search history.

(56) References Cited

U.S. PATENT DOCUMENTS

| | | | | |
|---|---|---|---|---|
| 5,097,132 A * | 3/1992 | Plummer | ............... | A61B 6/037 250/363.08 |
| 5,107,121 A * | 4/1992 | Lim | ................. | G01T 1/1648 250/363.04 |
| 8,505,137 B1 | 8/2013 | Gaines, Jr. | | |
| 2002/0039403 A1* | 4/2002 | Oota | ..................... | A61B 6/032 378/4 |
| 2003/0095635 A1* | 5/2003 | Moritake | ............... | A61B 6/035 378/198 |
| 2004/0206880 A1* | 10/2004 | Henley | ................ | F16M 11/048 248/675 |
| 2010/0142669 A1* | 6/2010 | Ren | ....................... | A61B 6/035 378/208 |
| 2011/0222667 A1* | 9/2011 | Gregerson | ............ | A61B 6/4435 378/198 |
| 2012/0189094 A1* | 7/2012 | Neushul | ................. | A61B 6/035 378/19 |
| 2012/0256099 A1* | 10/2012 | Gregerson | ............. | A61B 6/035 378/4 |
| 2012/0328077 A1* | 12/2012 | Bouvier | ................. | A61B 6/547 901/1 |
| 2014/0037071 A1* | 2/2014 | Foerner | ................ | A61B 6/4435 378/193 |
| 2014/0275953 A1* | 9/2014 | Gregerson | ........... | A61B 6/4405 600/407 |
| 2015/0124939 A1* | 5/2015 | Ahn | ..................... | A61B 6/4452 378/167 |
| 2015/0320376 A1* | 11/2015 | Oishi | ..................... | A61B 6/4488 378/199 |
| 2018/0184994 A1* | 7/2018 | Keertikumar | .......... | A61B 6/035 |
| 2018/0235552 A1* | 8/2018 | Aoki | ..................... | A61B 6/4429 |
| 2018/0289339 A1* | 10/2018 | Fortuna | ................ | A61B 6/4241 |
| 2018/0353143 A1* | 12/2018 | Gregerson | ............. | A61B 6/032 |

* cited by examiner

TRANSLATION DRIVE SYSTEM FOR AN IMAGING SYSTEM

PRIORITY CLAIM

This application is a U.S. National Phase Application of PCT/US2019/057755 filed on Oct. 24, 2019, which claims the benefit of U.S. Provisional Application No. 62/769,088 filed on Nov. 19, 2018, and U.S. Provisional Application No. 62/769,101 filed on Nov. 19, 2018, both of which are incorporated herein by reference in their entirety and to which this application claims the benefit of priority.

TECHNICAL FIELD

Aspects of the present invention relate to a translation drive system for an imaging system having an imaging gantry and a base, and more particularly, to a translation drive system that includes at least one upper rail affixed to the imaging gantry and at least one lower rail affixed to the base and front and lower carriages moveably attached to the lower rail wherein the upper rail is moveably attached to an upper carriage to enable movement of the imaging gantry relative to the base wherein when a lower carriage rear surface contacts a stop, the upper rail moves horizontally past a base rear surface into an extended position wherein the imaging gantry extends horizontally beyond the base rear surface.

BACKGROUND

Medical imaging systems such as those utilizing computed tomography (CT) or magnetic resonance imaging (MRI) technologies require precise (i.e. sub millimeter) translation drive systems to perform accurate sets of tomographic images of the patient. Such translation drive systems are normally coupled with a patient table wherein the patient is translated precisely through an imaging bore of the system. Many translation drive systems include numerous components such as motors, gears, pulleys, feedback sensors, etc. which provide a drive motion that is coupled to the actual load through one or more belts and/or chains. This creates a complex system that must be precisely tuned and/or calibrated to achieve the required accuracy since the belts are susceptible to stretching and the drive mechanisms have inherent backlash. In addition, such complex translation drive mechanisms occupy a substantial amount of space.

With respect to a portable CT imaging system, on the other hand, the CT imaging system is translated whereas the patient remains stationary. This presents several challenges for the translation drive system used for such imaging systems. In particular, the translation drive system for a portable CT imaging system must precisely translate a substantially heavier load. In addition, the center of gravity is located higher than the translation drive system which hinders the ability to provide the desired precision. Further, the CT imaging system may be mounted in an emergency transport vehicle such as an ambulance or rescue vehicle oriented in a relatively steep incline (i.e. +/−approximately 20 degrees). It is substantially more difficult for the translation drive system to achieve a desired precision since loads on the translation drive system shift due to gravity. Portable imaging systems that include a translation capability include a system base that is substantially the same size as the maximum translation distance. It is desirable to reduce the size of the system base and provide a mechanism that enables a greater translation distance for the imaging system than that provided by the size of the system base.

SUMMARY OF THE INVENTION

A translation drive system for an imaging system having an imaging gantry and a gantry base. The system includes at least one upper rail affixed to the imaging gantry and at least one lower rail affixed to the base, wherein the lower rail includes a stop. The system also includes front and lower carriages moveably attached to the lower rail wherein the upper rail is moveably attached to an upper carriage to enable movement of the imaging gantry relative to the base. Further, the system includes an extension spring attached between the lower carriage and the imaging gantry wherein when a lower carriage rear surface contacts the stop, the upper rail moves horizontally past a base rear surface into an extended position wherein the imaging gantry extends horizontally beyond the base rear surface. The system also includes a linear actuator that moves the imaging gantry.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which.

To facilitate understanding, identical reference numerals have been used, where possible, to designate identical elements that are common to the figures. The figures are not drawn to scale.

DETAILED DESCRIPTION

Figure 1:
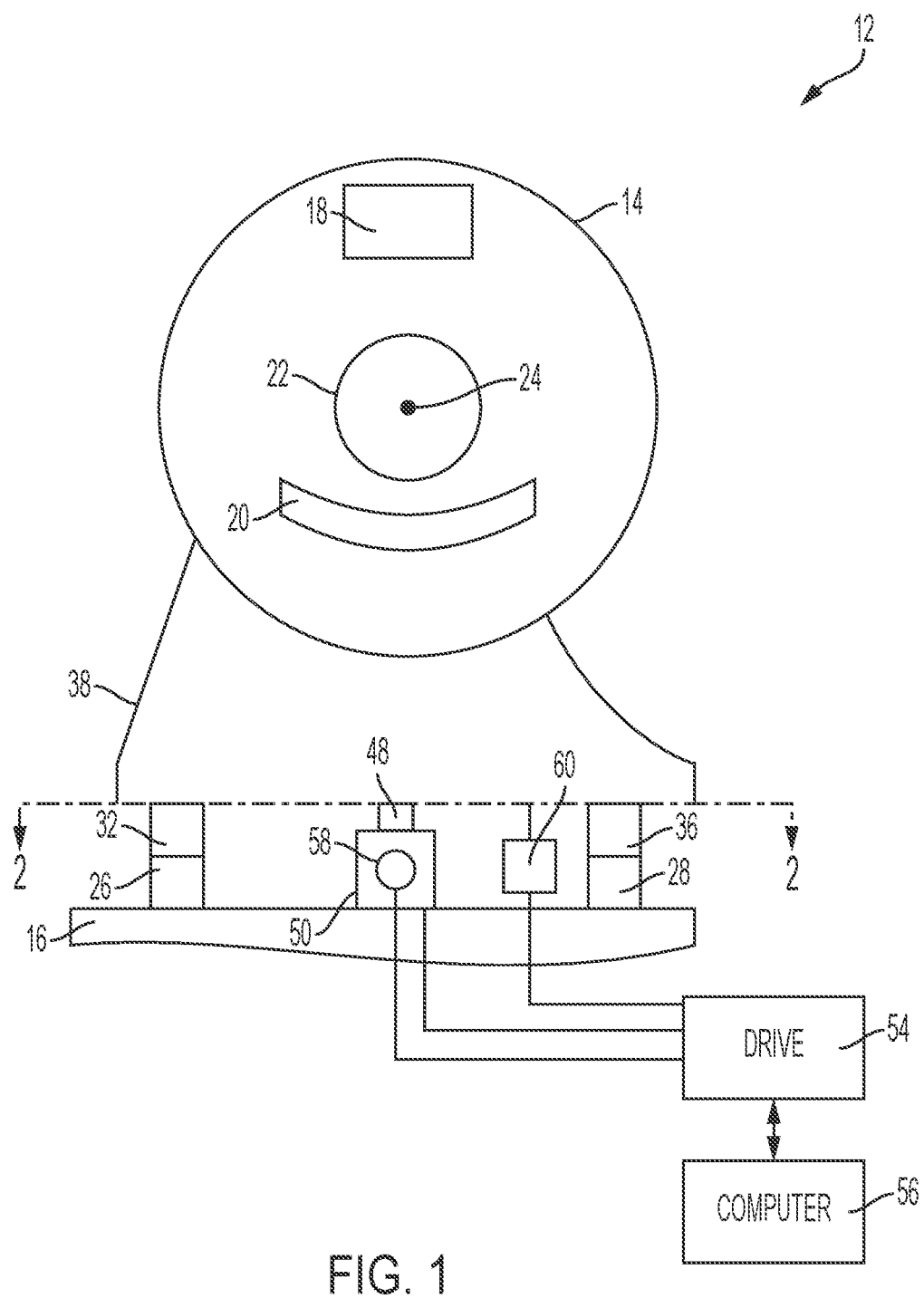
FIG. 1 is a top view of a direct translation drive system for an imaging system in accordance with an aspect of the invention.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Figure 2:
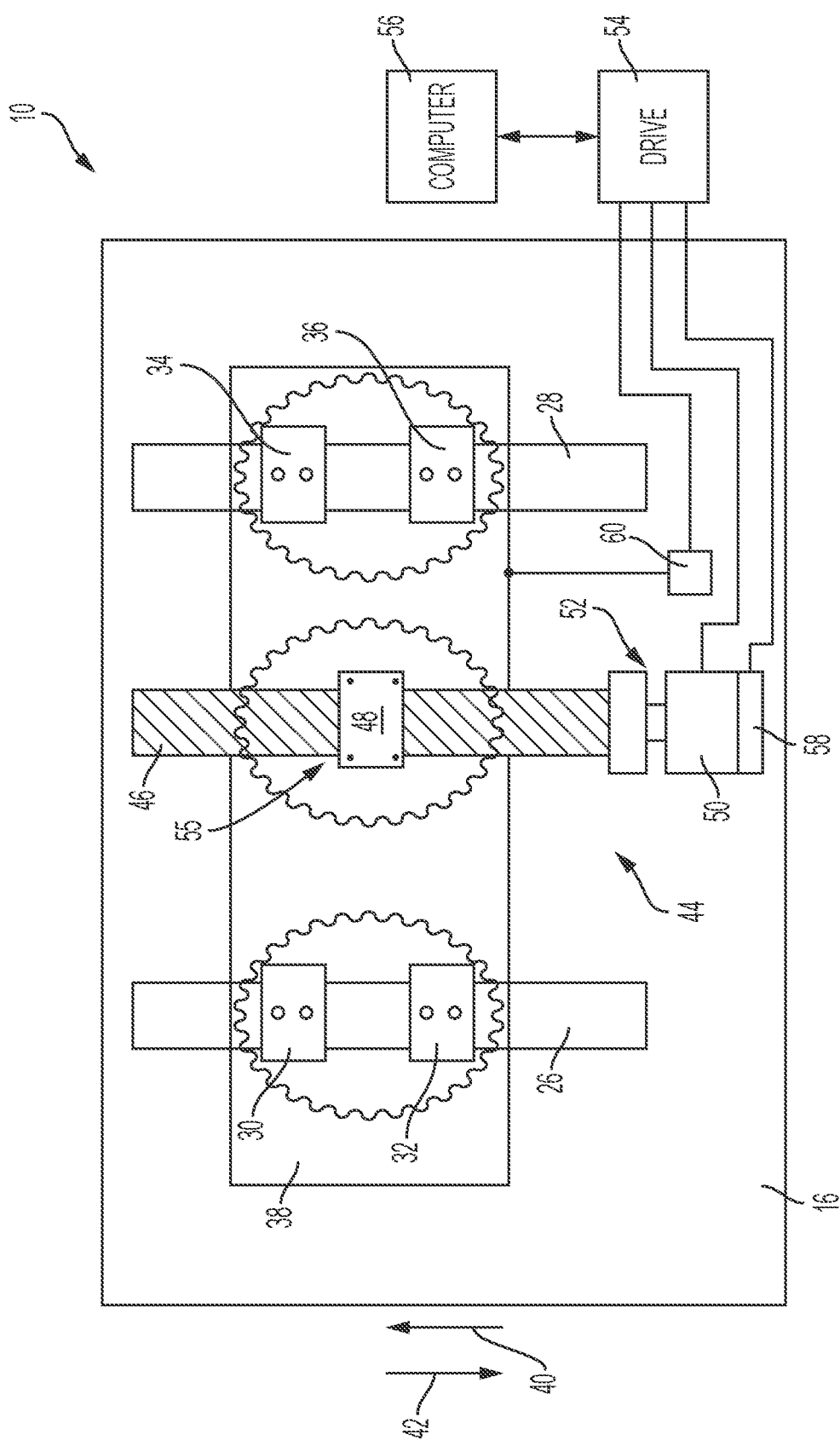
FIG. 2 is an end view of the drive system and an imaging system along view line 2-2 of FIG. 1.

Referring to FIG. 1, an end view of a direct translation drive system 10 for an imaging system 12 is shown. Referring to FIG. 2, a top view of the drive system 10 and along view line 2-2 of FIG. 1 is shown. Referring to FIG. 1 in conjunction with FIG. 2, imaging system 12 may be a portable imaging system having a moveable imaging gantry 14 and a single stationary gantry base 16 located underneath the imaging gantry 14. For example, the imaging gantry 14 may include computed tomography (CT) scanning apparatus such as a rotating X-ray generator 18, an X-ray detector 20 and various associated electronic hardware and software for controlling the apparatus and processing acquired data so as to generate CT images. The imaging gantry 14 also includes a patient bore 22 for receiving a patient. A center of gravity 24 for the imaging gantry 14 is located in the patient bore 22. Alternatively, the imaging gantry 14 may be a magnetic resonance imaging (MRI) scanner, positron emission tomography (PET) scanner, single-photon emission computerized tomography (SPECT) scanner, an X-ray scanner, or use surgery or interventional technologies.

The drive system 10 includes at least one elongated slide rail affixed to the base 16. In an embodiment, the drive system 10 includes first 26 and second 28 spaced apart stationary lower slide rails affixed to the base 16. The first 26 and second 28 lower rails each include at least one moveable carriage. In an embodiment, first 30 and second 32 lower carriages (shown in partial cross-sectional views) are moveably attached to the first lower rail 26 to enable movement of the first 30 and second 32 lower carriages relative to the first lower rail 26. In addition, third 34 and fourth 36 lower carriages are moveably attached to the second lower rail 28 to enable movement of the third 34 and fourth 36 lower carriages relative to the second lower rail 28. In an aspect of the invention, the lower carriages 30, 32, 34, 36 are each attached to a bottom support element 38 of the imaging gantry 14 to enable linear movement, or translation, of the imaging gantry 14 in a first direction 40 substantially parallel to the first 26 and second 28 rails and in a second direction 42 opposite the first direction 40. In accordance with an embodiment of the invention, translation of the imaging gantry 14 enables scanning of a patient to provide tomographic images of the patient. The first 26 and second 28 lower rails are located relative to the center of gravity 24 such that the first 26 and second 28 lower rails each support the weight of the imaging gantry 14 equally. This assists in enabling precise translation of the imaging gantry 14 by the drive system 10.

The drive system 10 also includes a single linear actuator 44 that moves the imaging gantry 14 relative to the first 26 and second 28 lower rails. In an embodiment, the linear actuator 44 includes a single ball screw 46 that threadably engages a ball screw nut 48 to form a ball screw mechanism 55. The ball screw nut 48 is attached to the bottom support element 38 of the imaging gantry 14. The drive system 10 further includes a motor 50, such as a stepper motor, attached to an end 52 of the ball screw 46. In addition, the drive system 10 includes a drive 54 coupled between the motor 50 and a computer 56 that controls the drive 54. In use, the motor 50 is energized by the drive 54 to cause either clockwise or counterclockwise rotation of the ball screw 46 relative to the ball screw nut 48. This, in turn, translates the ball screw nut 48 and thus the attached imaging gantry 14 in either the first 40 or second 42 directions to enable scanning of the patient. In an embodiment, a large diameter, small pitch precision ball screw 46 is used in order to provide sufficient mechanical advantage for precisely moving the imaging gantry 14 when oriented in a relatively steep incline (for example, approximately +/−20 degrees). In an aspect of the invention, the invention enables the use of a relatively small motor 50.

The motor 50 includes a first encoder 58 that detects a rotary position of the ball screw 46 and thus the imaging gantry 14 as the imaging gantry 14 is translated. The drive system 10 may also include a second encoder 60 connected to the imaging gantry 14 to directly measure a position of the imaging gantry 14. It understood that other linear actuators may be used such as a linear motor, an electromechanical actuator and others to move the imaging gantry 14. In accordance with an aspect of the invention, the ball screw 46, ball screw nut 48, motor 50, first 58 and second 60 encoders, first 26 and second 28 lower rails and lower carriages 30, 32, 34, 36 are located in a single base 16 located underneath the imaging gantry 14. Thus, in accordance with another aspect of the invention, the imaging gantry 14 is translated by using only a single linear actuator 44, such as ball screw 46 and associated ball screw nut 48, located in the single base 16.

Figure 3:
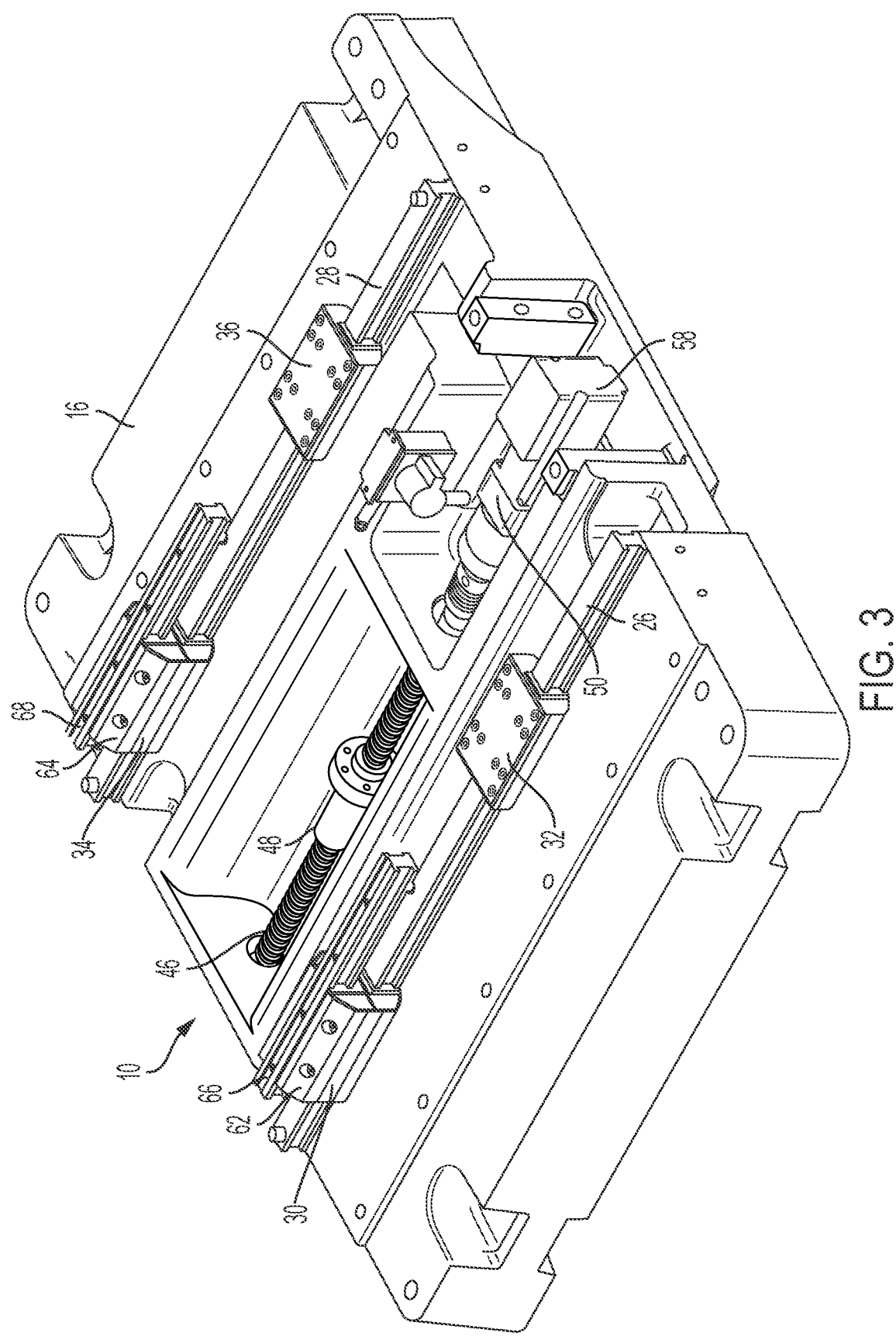
FIG. 3 is a perspective view of the drive system and base.

Referring to FIG. 3, a perspective view of the drive system 10 and base 16 is shown. In accordance with an aspect of the invention, selected carriages, for example the first lower 30 and third lower 34 carriages, are attached to first 62 and second 64 upper carriages, respectively. First 66 and second 68 upper slide rails are affixed to the bottom support element 38 and extend downward from the bottom support element 38. The first 66 and second 68 upper rails are moveably attached to the first 62 and second 64 upper carriages, respectively. As will be described, the first 66 and second 68 upper rails are moveable to an extended position wherein the upper rails 66, 68 extend horizontally beyond the base 16 to enable corresponding translation of the imaging gantry 14 beyond the base 16.

Figure 4:
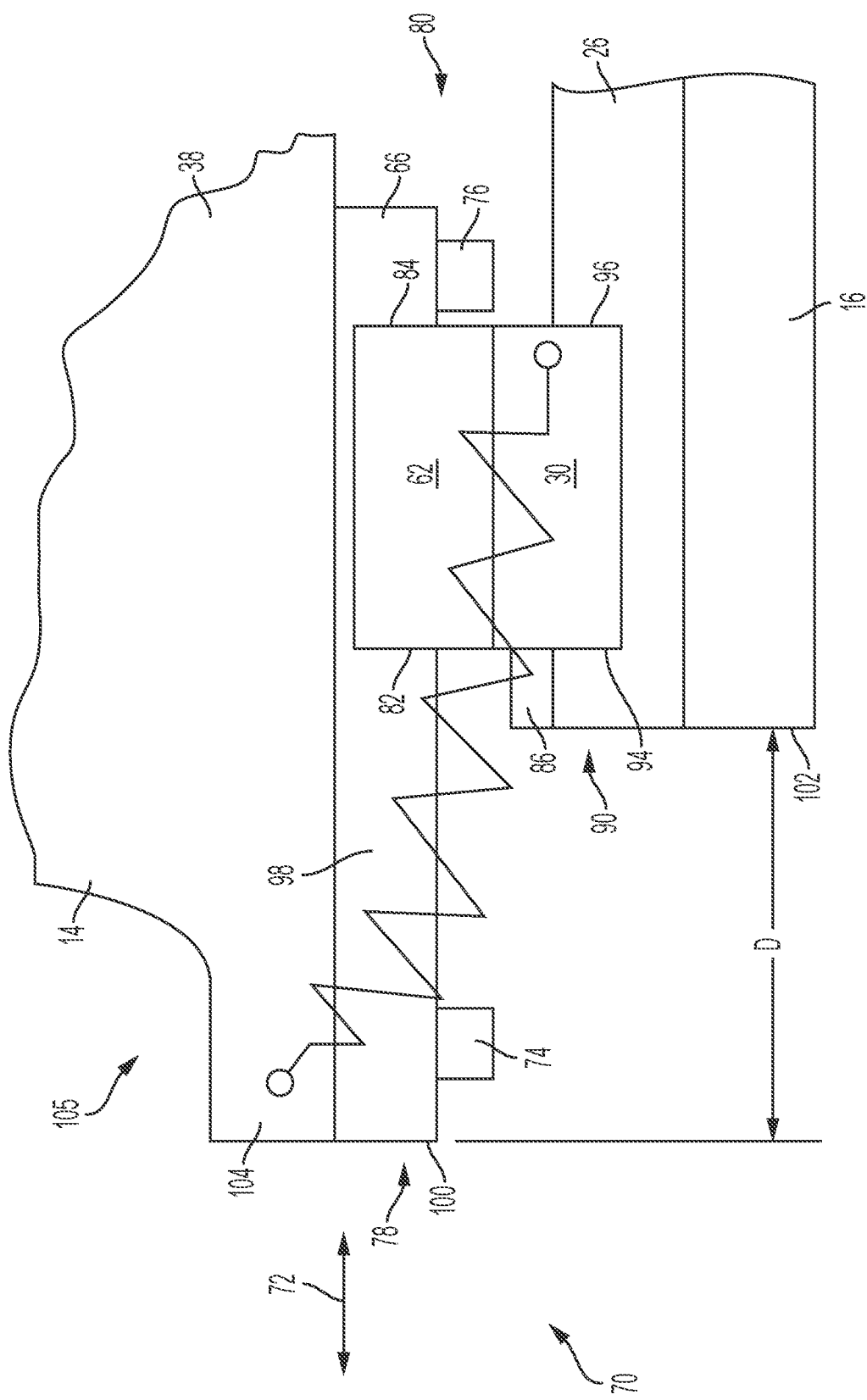
FIG. 4 is a partial side view of a linear extension mechanism showing an upper rail in an extended position and an imaging gantry extending horizontally beyond a rear surface of a gantry base.
Figure 5:
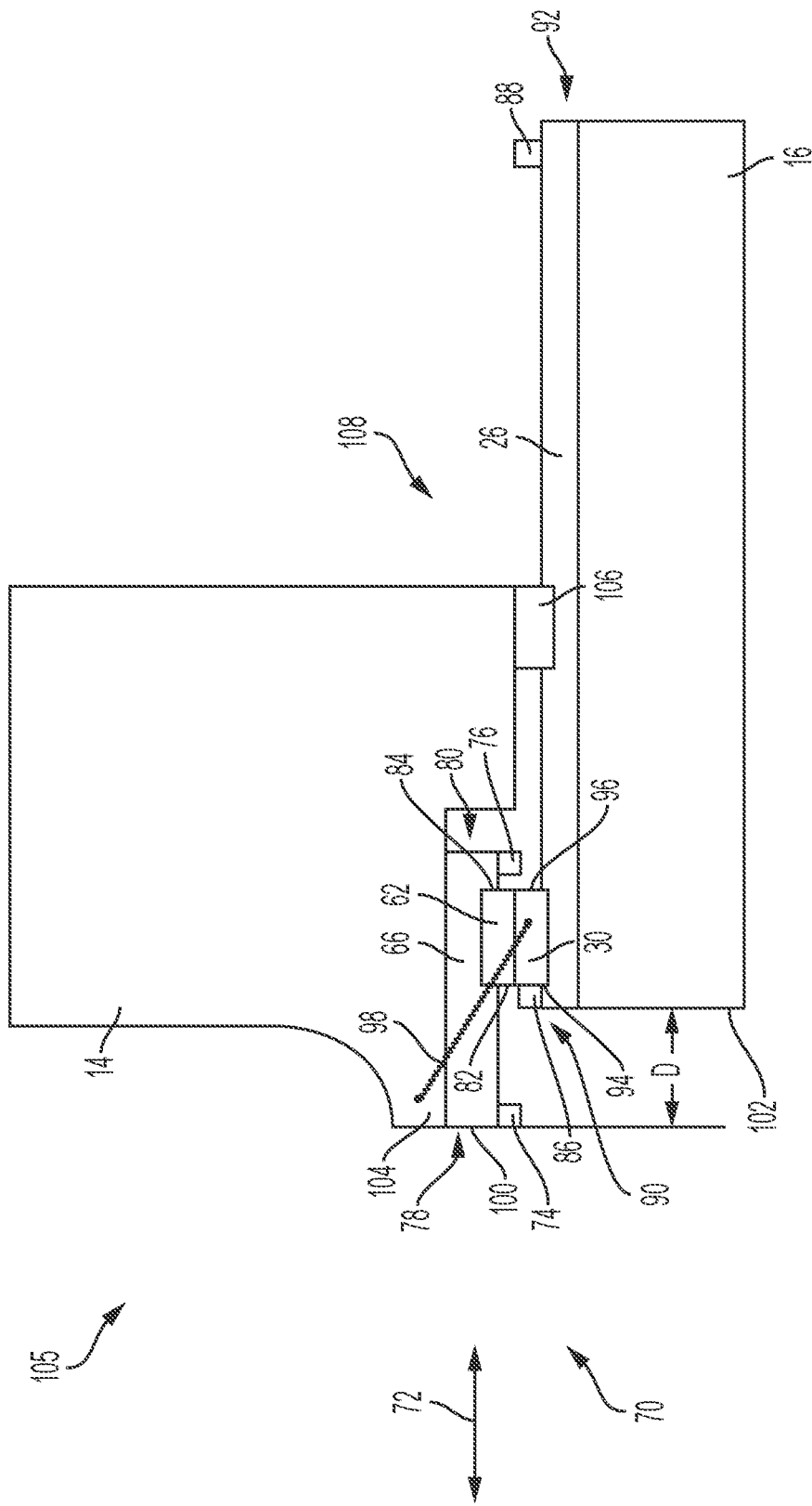
FIG. 5 is an overall side view of the extension mechanism, the imaging gantry and gantry base in a rearmost position.

FIG. 4 depicts a partial side view of a first linear extension mechanism 70 for the drive system 10 in accordance with an aspect of the invention. FIG. 4 depicts the first upper carriage 62 and attached first lower carriage 30 described in connection with FIG. 3. As previously described, the first upper 66 and first lower 26 rails are affixed to the bottom support element 38 of the imaging gantry 14 and the base 16, respectively, of the portable imaging system 12 wherein the imaging gantry 14 is translated and the base 16 is stationary. The first lower carriage 30 is moveably attached to the first lower rail 26 to enable movement of the carriages 62, 30 in a horizontal direction 72 relative to the first lower rail 26. The first upper rail 66 is moveably attached to the first upper carriage 62 to enable movement of the first upper rail 66 in the horizontal direction 72 relative to the carriages 62, 30 and the first lower rail 26. The first upper carriage 62 is located between spaced apart first 74 and second 76 upper stop elements located at rear 78 and front 80 ends, respectively, of the first upper rail 66. Referring to FIG. 5 in conjunction with FIG. 4, the first lower carriage 30 is located between spaced apart third 86 and fourth 88 stop elements located at rear 90 and front 92 ends, respectively, of the first lower rail 26. In an aspect, the stops 86, 88 ensure that the first lower carriage 30 does not slide off the first lower rail 26 and stops 74, 76 ensure that the first upper carriage 62 does not slide off the first upper rail 66. In an embodiment, the stops 74, 76, 86, 88 may be fabricated from a resilient material such as rubber.

An extension spring 98 is attached between the first lower carriage 30 and the imaging gantry 14. In FIG. 4, the first upper rail 66 is shown moved to an extended position wherein a rail rear surface 100 of the first upper rail 66 extends horizontally beyond a base rear surface 102 of the base 16 by a horizontal distance D, thus extending the spring 98. In the extended position, the third stop 86 also contacts the lower carriage rear surface 94. Movement of the first upper rail 66 to the extended position causes corresponding horizontal movement of the imaging gantry 14 relative to the base rear surface 102 such that a rear surface 104 of the imaging gantry 14 extends horizontally beyond the base rear surface 102, thus locating the imaging gantry 14 in a rearmost position 105. In an embodiment, the rail rear surface 100 is aligned with the imaging gantry rear surface 104 such that the imaging gantry rear surface 104 extends horizontally beyond the base rear surface 102 by the distance D.

Figure 6:
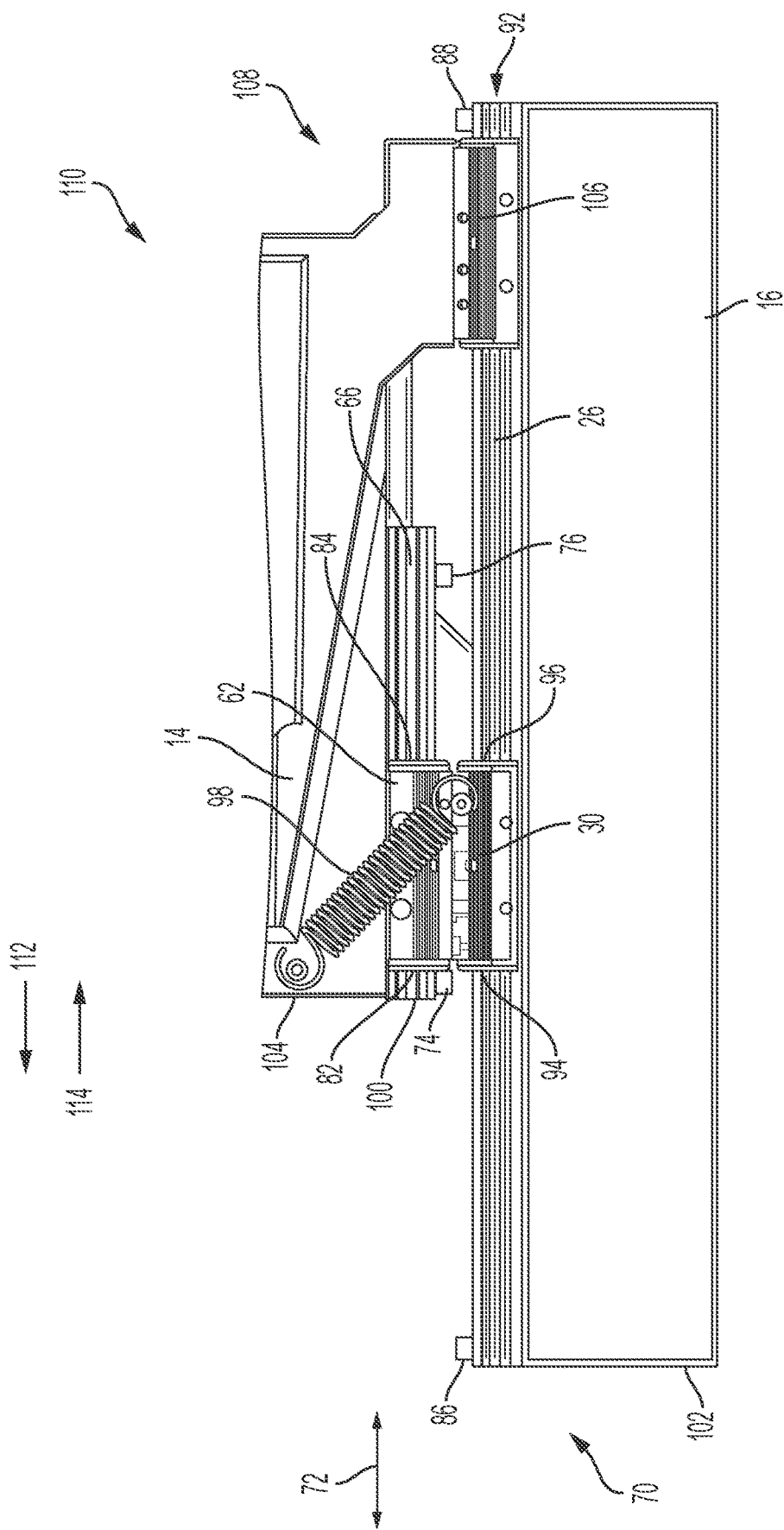
FIG. 6 depicts the imaging gantry in a frontmost position.

Referring to FIG. 5, an overall side view of the first extension mechanism 70, imaging gantry 14 and base 16 is shown. The first extension mechanism 70 also includes a front carriage 106 that is moveably attached to the first lower rail 26 and located between the first lower carriage 30 and the fourth stop 88. A front portion 108 of the imaging gantry 14 is attached to the front carriage 106. Thus, the imaging gantry 14, first upper rail 66, carriages 62, 30 and front carriage 106 are moveable relative to the first lower rail 26 and base 16 in the horizontal direction 72. Referring to FIG. 6, the imaging gantry 14 is shown located in a frontmost position 110 wherein the front carriage 106 is located adjacent the fourth stop 88 such that a distance traveled by the imaging apparatus between the frontmost 110 and rearmost 105 positions is sufficient to enable scanning of the patient by scanning apparatus. In addition, spring tension generated by the spring 98 causes contact between the upper carriage rear surface 82 and the first stop 74.

In an embodiment of the invention, the imaging gantry 14 is attached to a drive element such as the linear actuator 44, motor drive or other device that causes linear movement of the imaging gantry 14 in the horizontal direction 72 between the frontmost 110 and rearmost 105 positions. An exemplary operation in accordance with an embodiment of the invention will now be described with reference to FIGS. 4-6. During rearward movement 112 of the imaging gantry 14 from the frontmost position 110, spring tension generated by the spring 98 maintains contact between the upper carriage rear surface 82 and the first stop 74 and prior to contact between the lower carriage rear surface 94 and the third stop 86. Thus, activation of the linear actuator 44 causes rearward movement 112 of the imaging gantry 14 which in turn causes corresponding rearward movement 112 of both carriages 62, 30 relative to the first lower rail 26 prior to contact between the lower carriage rear surface 94 and the third stop 86.

Movement of the carriages 62, 30 subsequently stops upon contact between the lower carriage rear surface 94 and the third stop 86. The imaging gantry 14 and first upper rail 66 then continue to move toward the rearmost position 105 wherein the first upper rail 66 moves past the base rear surface 102 and into the extended position. In the extended position, the rail rear surface 100 and imaging gantry rear surface 104 both extend horizontally beyond the base rear surface 102, thus extending the spring 98 as previously described. In an embodiment, the imaging gantry rear surface 104 extends beyond the base rear surface 102 by the horizontal distance D. Thus, the extension mechanism 70 of the invention provides a translation distance for the imaging gantry 14 that is greater than the size of the base 16. Further, an aspect of the invention enables a reduction in the size of the base 16 to provide a portable imaging system 12 having increased space efficiency.

In order to return the imaging gantry 14 back to the frontmost position 110, the imaging gantry 14 is moved in an opposite (forward) direction 114 by the linear actuator 44. As the imaging gantry 14 moves forward, contact occurs between the first stop 74 and the upper carriage rear surface 82. The first stop 74 then pushes the carriages 62, 30 in the forward direction 114 as the imaging gantry 14 moves forward until the imaging gantry 14 is in the frontmost position 110.

In accordance with an aspect of the invention, a second extension mechanism 70 is used in conjunction with the second lower rail 28 to move the imaging gantry 14 between the rearmost 105 and frontmost 110 positions. In particular, the second extension mechanism 70 includes a first upper rail 66, first upper 62 and first lower 30 carriages, front carriage 106, spring 98 and stops 74, 76, 86, 88 and associated elements wherein the first lower carriage 30 and front carriage 106 are both moveably attached second lower rail 28. Further, the extension mechanism 70 is located in the base 16.

In an aspect of the invention, a precision drive system 10 is provided having a reduced number of components thus enabling a reduction in size of the base 16. In addition, the drive system 10 of the invention may be easily assembled and is rugged. Further, the drive system 10 avoids the disadvantages associated with conventional translation drive systems such as complexity, backlash and the need to calibrate the translation drive system. In another aspect of the invention, an extension mechanism 70 is provided that enables a translation distance for the imaging gantry 14 that is greater than the size of the base 16 thus also enabling a reduction in size of the base 16 to provide a portable imaging system 12 having increased space efficiency.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A translation drive system for an imaging system having an imaging gantry and a gantry base, comprising:
at least one upper rail affixed to the imaging gantry, wherein the upper rail includes a first stop;
at least one lower rail affixed to the gantry base, wherein the lower rail includes a second stop;
front and lower carriages moveably attached to the lower rail, wherein the upper rail is moveably attached to an upper carriage to enable movement of the imaging gantry relative to the gantry base, and wherein the upper and lower carriages include upper and lower carriage rear surfaces, respectively;
an extension spring attached between the lower carriage and the imaging gantry, wherein spring tension generated by the spring maintains contact between the upper carriage rear surface and the first stop, wherein when the lower carriage rear surface contacts the second stop, the upper rail moves horizontally past a base rear surface into an extended position, and wherein the imaging gantry extends horizontally beyond the base rear surface; and
a linear actuator attached to the imaging gantry, wherein upon actuation of the linear actuator the imaging gantry is translated in either a first direction or a second direction opposite the first direction relative to the gantry base.

2. The translation drive system according to claim 1, wherein the upper carriage is affixed to the lower carriage.

3. The translation drive system according to claim 1, wherein the first stop is located at an end of the upper rail.

4. The translation drive system according to claim 1, wherein the second stop is located at an end of the lower rail.

5. The translation drive system according to claim 1, wherein the linear actuator includes a ball screw that threadably engages a ball screw nut attached to the imaging gantry.

6. The translation drive system according to claim 1, wherein the linear actuator includes a motor.

7. The translation drive system according to claim 1, further including at least one encoder for determining a position of the imaging gantry.

8. The translation drive system according to claim 1, wherein first and second lower slide rails are attached to the gantry base.

9. The translation drive system according to claim 1, wherein the linear actuator, the upper and lower rails, the upper and lower carriages, the front carriage and the extension spring provide an arrangement that results in a reduction in a size of the gantry base to provide a portable imaging system having increased space efficiency.

10. A translation drive system for an imaging system having an imaging gantry and a gantry base, comprising:
at least one upper rail affixed to the imaging gantry, wherein the upper rail includes a first stop;
at least one lower rail affixed to the gantry base, wherein the lower rail includes a second stop;
front and lower carriages moveably attached to the lower rail, wherein the upper rail is moveably attached to an upper carriage affixed to the lower carriage to enable movement of the imaging gantry relative to the gantry base, and wherein the upper and lower carriages include upper and lower carriage rear surfaces, respectively;
an extension spring attached between the lower carriage and the imaging gantry, wherein spring tension generated by the spring maintains contact between the upper carriage rear surface and the first stop prior to contact between the lower carriage rear surface and the second stop, wherein when the lower carriage rear surface contacts the second stop, the upper rail moves horizontally past a base rear surface into an extended position, and wherein the imaging gantry extends horizontally beyond the base rear surface by a first distance; and
a single linear actuator located in the gantry base and attached to the imaging gantry, wherein upon actuation of the linear actuator the imaging gantry is translated in either a first direction or a second direction opposite the first direction relative to the gantry base.

11. The translation drive system according to claim 10, wherein the first stop is located at an end of the upper rail.

12. The translation drive system according to claim 10, wherein the second stop is located at an end of the lower rail.

13. The translation drive system according to claim 10, wherein the linear actuator includes a ball screw that threadably engages a ball screw nut attached to the imaging gantry.

14. The translation drive system according to claim 10, wherein the linear actuator includes a motor.

15. The translation drive system according to claim 10, further including at least one encoder for determining a position of the imaging gantry.

16. A method of moving an imaging gantry relative to a gantry base, comprising:
providing at least one upper rail affixed to imaging gantry, wherein the upper rail includes a first stop;
providing at least one lower rail affixed to the gantry base, wherein the lower rail includes a second stop;
providing front and lower carriages moveably attached to the lower rail, wherein the upper rail is moveably attached to an upper carriage to enable movement of the imaging gantry relative to the gantry base, and wherein the upper and lower carriages include upper and lower carriage rear surfaces, respectively;
providing an extension spring attached between the lower carriage and the imaging gantry, wherein spring tension generated by the spring maintains contact between the upper carriage rear surface and the first stop; and
providing a linear actuator that moves the imaging gantry and upper and lower carriages in a horizontal direction wherein when the lower carriage rear surface contacts the second stop, the upper rail moves horizontally past a base rear surface into an extended position, and wherein the imaging gantry extends horizontally beyond the base rear surface.

17. The method according to claim 16, wherein the upper carriage is affixed to the lower carriage.

18. The method according to claim 16, wherein the first stop is located at an end of the upper rail.

19. The method according to claim 16, wherein the second stop is located at an end of the lower rail.

20. The method according to claim 16, wherein the linear actuator includes a ball screw that threadably engages a ball screw nut attached to the imaging gantry.

\* \* \* \* \*